United States Patent
Virmani et al.

(10) Patent No.: US 9,474,449 B2
(45) Date of Patent: *Oct. 25, 2016

(54) SINGLE SCAN MULTI-PROCEDURE IMAGING

(71) Applicant: KONINKLIJKE PHILIPS N.V., Eindhoven (NL)

(72) Inventors: Sunny Virmani, Twinsburg, OH (US); Thomas John Naypauer, Cleveland Heights, OH (US); Douglas B. McKnight, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 84 days.

This patent is subject to a terminal disclaimer.

(21) Appl. No.: 14/558,754

(22) Filed: Dec. 3, 2014

(65) Prior Publication Data

US 2015/0087999 A1    Mar. 26, 2015

Related U.S. Application Data

(63) Continuation of application No. 14/061,985, filed on Oct. 24, 2013, now Pat. No. 8,934,696, which is a continuation of application No. 13/321,208, filed as application No. PCT/IB2010/052126 on May 12, 2010, now Pat. No. 8,594,406.

(60) Provisional application No. 61/218,090, filed on Jun. 18, 2009, provisional application No. 61/237,334, filed on Aug. 27, 2009.

(51) Int. Cl.
*A61B 5/00* (2006.01)
*G06F 19/00* (2011.01)
(Continued)

(52) U.S. Cl.
CPC .............. *A61B 5/0084* (2013.01); *A61B 1/31* (2013.01); *A61B 5/0035* (2013.01); *A61B 5/02007* (2013.01); *A61B 5/4509* (2013.01); *A61B 5/4872* (2013.01); *A61B 6/032* (2013.01); *A61B 6/461* (2013.01); *A61B 6/463* (2013.01); *A61B 6/467* (2013.01); *A61B 6/504* (2013.01); *A61B 6/505* (2013.01); *A61B 6/5217* (2013.01); *G06F 19/321* (2013.01); *G06F 19/3406* (2013.01);
(Continued)

(58) Field of Classification Search
None
See application file for complete search history.

(56) References Cited

U.S. PATENT DOCUMENTS

| 6,137,858 A | 10/2000 | Horiuchi |
| 6,205,348 B1 * | 3/2001 | Giger ............... A61B 6/482 382/128 |

(Continued)

FOREIGN PATENT DOCUMENTS

| EP | 0985379 A1 | 3/2000 |
| EP | 1387320 A2 | 2/2004 |

(Continued)

OTHER PUBLICATIONS

Birk, S.; CT Colonography detects bone loss; 2008; Internal Medicine News; 2 pages.

(Continued)

*Primary Examiner* — Siamak Harandi

(57) ABSTRACT

A method includes receiving a signal indicative of a single user selected imaging protocol for scanning a patient. The imaging protocol includes parameters for two or more of a bone mineral density, a fat composition, or an aortic calcium imaging procedures. The method further includes performing a single scan of the patient using the single user selected protocol. The method further includes generating a single set of image data for the two or more of a bone mineral density, a fat composition, or an aortic calcium imaging procedures.

20 Claims, 2 Drawing Sheets

(51) Int. Cl.
  *A61B 6/03* (2006.01)
  *A61B 6/00* (2006.01)
  *A61B 5/02* (2006.01)
  *A61B 1/31* (2006.01)
  *G06T 1/00* (2006.01)
  *G06T 7/00* (2006.01)

(52) U.S. Cl.
  CPC ........... *G06T 1/0007* (2013.01); *G06T 7/0012* (2013.01); *A61B 5/4255* (2013.01); *A61B 6/465* (2013.01); *A61B 2576/02* (2013.01)

(56) References Cited

U.S. PATENT DOCUMENTS

| | | |
|---|---|---|
| 6,529,954 B1 | 3/2003 | Cookmeyer, II et al. |
| 6,922,462 B2 | 7/2005 | Acharya et al. |
| 2003/0194120 A1 | 10/2003 | Unger et al. |
| 2004/0101086 A1 | 5/2004 | Sabol et al. |
| 2007/0041490 A1 | 2/2007 | Jha et al. |
| 2008/0082002 A1 | 4/2008 | Wilson et al. |
| 2008/0118020 A1 | 5/2008 | Thibault et al. |
| 2009/0279672 A1 | 11/2009 | Reiner |

FOREIGN PATENT DOCUMENTS

| | | |
|---|---|---|
| EP | 1736102 A2 | 12/2006 |
| JP | H08166995 A | 6/1996 |
| JP | 2004113644 A | 4/2004 |
| JP | 2004208715 A | 7/2004 |
| JP | 2008073239 A | 4/2008 |
| WO | 2006101993 A2 | 9/2006 |

OTHER PUBLICATIONS

RSNA; 2008; Assessment of bone Mineral Density on CT; http://rsna2008.rsna.org/customcf/conference/event_display.cfm?em_id=6014550&pr.

RSNA; 2008; CT Colonography Offers One-Stop Screening for Cancer and Osteoporosis; http://rsna.org/media/pressreleases/PDF/pressreleasePDF.cfm?ID=387.

* cited by examiner

SINGLE SCAN MULTI-PROCEDURE IMAGING

CROSS REFERENCE TO RELATED APPLICATIONS

This application is a continuation of U.S. patent application Ser. No. 14/061,985 filed Oct. 24, 2013 which is a continuation of U.S. patent application Ser. No. 13/321,208 filed Nov. 18, 2011 which is a national filing of PCT application Serial No. PCT/IB2010/052126, filed May 12, 2010, published as WO 2010/146484 A1 on Dec. 23, 2010, which claims the benefit of U.S. provisional application Ser. No. 61/218,090 filed Jun. 18, 2009 and U.S. provisional application Ser. No. 61/237,334 filed Aug. 27, 2009, both of which are incorporated herein by reference.

DESCRIPTION

The following generally relates to imaging, and finds particular application to computed tomography (CT) imaging, and more particularly to a single scan with a protocol that is based on a plurality of different imaging procedures, and processing the imaging data and/or presenting and/or reporting on the processed imaging data. However, it is also amenable to other medical imaging applications and to non-medical imaging applications.

A computed tomography (CT) scanner generally includes an x-ray tube that emits radiation that traverses an examination region and a patient supported therein via a patient support. A detector array detects radiation traversing the examination region and the patient. The detector array generates a signal indicative of the detected radiation. A reconstructor reconstructs the signal and generates volumetric image data indicative of the patient. The volumetric image data can be processed to generate one or more images of the patient. The one or more images can be displayed on a monitor and/or printed to film.

Generally, one or more anatomy specific scanning protocols are generated for a plurality of different anatomical structures. By way of example, one or more protocols are designed specifically for bone scans while one or more other protocols are designed for soft tissue scans such as a scan of liver or brain. Each protocol is configured with scan parameters values based on the particular anatomical structure. Examples of such scan parameters include mA, kVp, slice thickness, resolution, number of slices, etc.

Unfortunately, when using such anatomy specific protocols a patient undergoing a soft tissue scan and a bone scan is often scanned and irradiated twice, once for the soft tissue scan and once for the bone scan, with each scan increasing the patient's lifetime radiation dose. In addition, the scans may be performed at two different times and/or locations with scan results from the first scan not readily accessible and separate from the results from the other scan. Moreover, an ordered scan such as some screening type scans (e.g., CT colonography) may not be performed due to the scan not being included on a pre-approved procedure list. In one instance, this may be due to a concern with irradiating patients with no symptoms.

Aspects of the present application address the above-referenced matters and others.

According to one aspect, a method includes receiving imaging data generated by an imaging system for a scan performed utilizing an imaging protocol with parameters that are based on a plurality of different imaging procedures. The method further includes processing the imaging data using at least one algorithm corresponding to at least one of the plurality of different imaging procedures. The method further includes presenting the processed imaging data.

According to another aspect, a system includes protocol bank for storing one or more imaging protocols. At least one of the protocols is based on a plurality of different imaging procedures. The system further includes an imaging system utilized to scan a patient based on the at least one protocol, wherein the imaging system generates imaging data indicative thereof. The system further includes an imaging data processor that processes the generated imaging data using at least one algorithm corresponding to at least one of the plurality of different imaging procedures. The system further includes a presentation component that presents the processed imaging data.

According to another aspect, a computer readable storage medium containing instructions which, when executed by a computer, cause the computer to perform the steps of: receiving imaging data acquired with an imaging protocol that is based on colonography, bone mineral density, fat assessment, and vascular calcium score imaging procedures; processing the imaging data using at least one algorithm corresponding to at least one of the imaging procedures, and presenting the processed imaging data.

According to another aspect, a method includes performing an imaging procedure using a protocol optimized for a plurality of different imaging procedures and generating imaging data, determining that the protocol satisfies at least one other imaging procedure, associating the imaging data with first indicia indicating that the imaging data satisfies the at least one other imaging procedure, and storing the imaging data and the first indicia in a first data repository.

The invention may take form in various components and arrangements of components, and in various steps and arrangements of steps. The drawings are only for purposes of illustrating the preferred embodiments and are not to be construed as limiting the invention.

Figure 1:
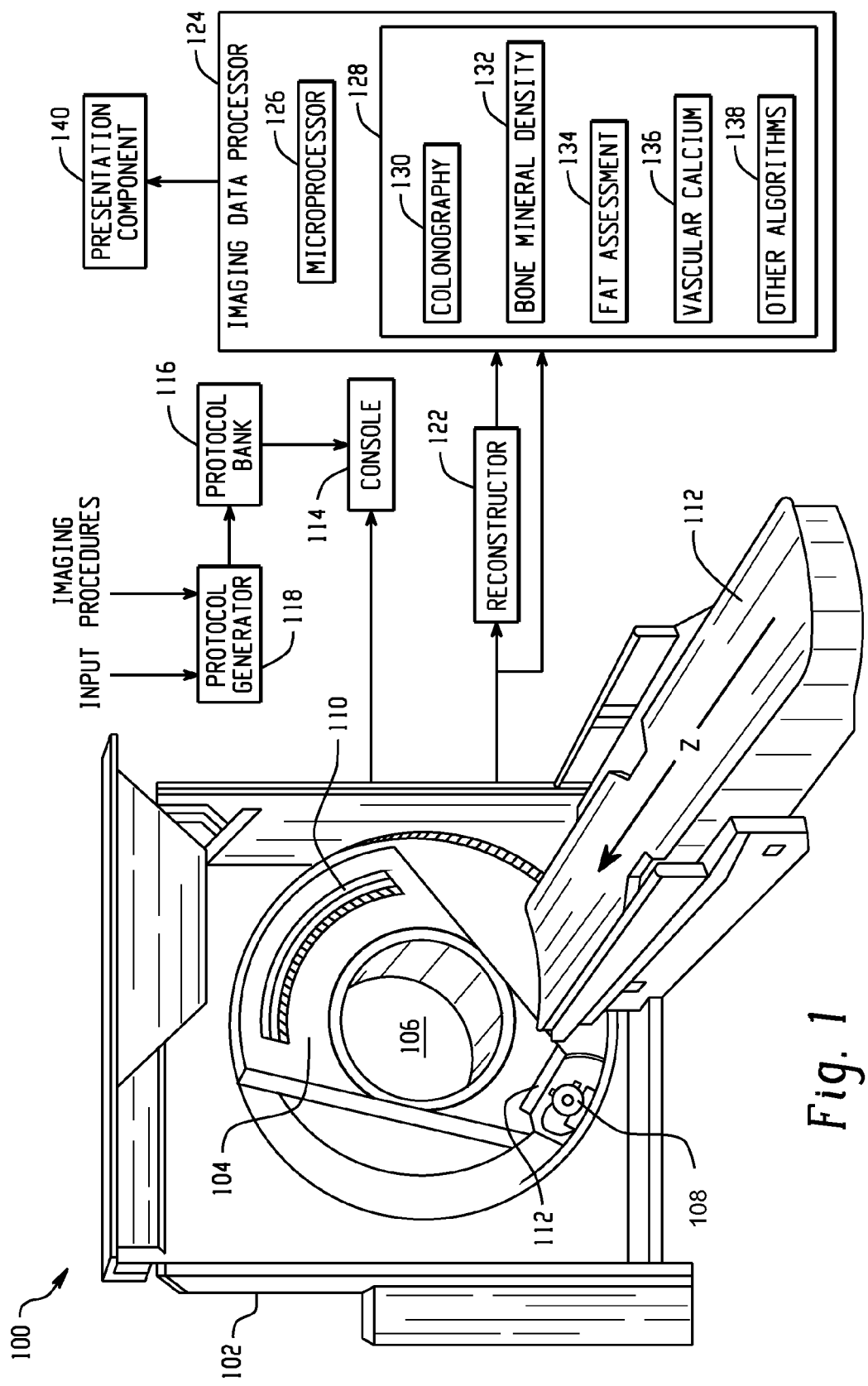
FIG. 1 illustrates an example imaging data analysis system in connection with an imaging system.

FIG. 1 illustrates an imaging system 100 such as a computed tomography (CT) scanner. The imaging system 100 includes a stationary gantry 102 and a rotating gantry 104, which is rotatably supported by the stationary gantry 102. The rotating gantry 104 rotates around an examination region 106 about a longitudinal or z-axis.

A radiation source 108, such as an x-ray tube, is supported by and rotates with the rotating gantry 104 around the examination region 106. The radiation source 108 emits radiation, and a collimator collimates the emitted radiation and produces a generally fan, wedge, or cone shaped radiation beam that traverses the examination region 106.

A radiation sensitive detector array 110 is also supported by the rotating gantry 104 and subtends an angular arc across from the radiation source 108, opposite the examination region 106. The detector array 110 detects radiation that traverses the examination region 106 and generates projection data indicative thereof.

A patient support 112, such as a couch, supports the patient in the examination region 106.

A general purpose computing system 114 serves as an operator console. The console includes at least one processor and software or computer executable instructions resident on a computer readable medium. The software, when executed by the processor or other processor, allows the operator to control operation of the system 100, including selecting an imaging protocol, creating an imaging protocol, modifying an imaging protocol, initiating scanner, transferring imaging data, etc.

A protocol bank 116 stores one or more scanning or imaging protocols for use by the system 100. At least one of the protocols in the protocol bank 116 is tailored for a set of different imaging procedures. For example, in one instance, at least one of the protocols is optimized for four (4) different imaging procedures, including colonography, bone mineral density, fat assessment, and vascular (e.g., aortic) calcium imaging procedures. In one instance, the protocol is optimized on the aggregate scan requirements of the different imaging procedures, as opposed to the scan requirements of an individual specific protocol. In another instance, a weighting factor (e.g., from 0 to 1) is used to focus or center the protocol on a subset of one or more of the different imaging procedures. Yet another protocol may be optimized for one or more different imaging procedures.

An example colonography scan includes an abdomen-pelvis scan with the patient's colon insufflated for interpretation of intra-colon abnormalities. An example bone mineral density scan includes an abdomen-pelvis scan with the results used to measure the bone density of a patient, for example, for osteoporosis screening/diagnosis. A fat assessment scan is used to measure visceral and/or subcutaneous fat. A vascular calcium scan is used to generate a vascular calcium score which indicates a presence and/or degree of vascular calcification.

By using a protocol generated based on a set of different imaging procedures for scanning, imaging data from a single scan be used for all four (colonography, bone mineral density, fat assessment, and vascular calcium) of the imaging procedures. As noted above, such a protocol may be optimized based on the aggregate of all of the imaging procedures, a weighted aggregate, a subset of the imaging procedures, or otherwise.

In one embodiment, the protocol bank 116 is a database (or the information therein may additionally be provided to a database), which is located locally or remotely to the console 114. In this embodiment, at least one protocol in the protocol bank 116 includes or is associated with information (e.g., metadata, flags, indicia, a look-up-table, etc.) that indicates which imaging procedure(s) it satisfies. This information is accessible to authorized personnel (e.g., refereeing physicians, radiologists, technicians, etc.) and can be used (as is or modified) for subsequent scanning. An executing console, web or other application can be used to search the database for candidate protocols for an imaging procedure based on various criteria such as patient information, imaging procedure(s) of interest, etc.

Similarly, the imaging data (and/or information derived therefom and/or processed imaging data) from the scans performed using such protocols can be tagged or associated with information that indicates which imaging procedure(s) it satisfies. The imaging data can be stored in a data repository such a Picture Archiving and Communication System (PACS), a Radiology Information System (RIS), a Hospital Information System (HIS), and/or data repository. Likewise, an executing console, web or other application can be used to search the data repository for prior imaging procedures based on criteria such as patient information, imaging procedure(s) of interest, imaging procedure(s) satisfied, etc. In one instance, this allows a physician to input a request for a new scanning procedure and determine if prior imaging scans include the data needed for the new scanning procedure. This may eliminate or replace the new scan procedure, or provide data for historical comparison.

A protocol generator 118 generates imaging protocols, including protocols stored in the protocol bank 116. The illustrated protocol generator 118 includes a processor that generates protocols based on a particular set of imaging procedures, such as those noted above, and user or other input. Where the set of imaging procedures includes colonography, bone mineral density, fat assessment, and vascular calcium imaging procedures, the protocol generator 118 can generate an imaging protocol that is optimized based on an aggregate, a weighted aggregate, a subset, etc. of the colonography, bone mineral density, fat assessment, and vascular calcium imaging procedures.

The input provided to the protocol generator 118 may include information such as which, if any, of the imaging procedures are for diagnostic purposes and/or which, if any, of the imaging procedures are for screening purposes. The protocol generator 118 can then take this information into account when generating a protocol. For example, such information may correlate to a particular weighting scheme where diagnostic imaging procedures are weighted higher than non-diagnostics imaging procedures. In another example, the protocol generator 118 may use a look up table or other predefined list to determined whether an imaging procedure is a diagnostic or screening imaging procedure.

A reconstructor 122 reconstructs the projection data and generates volumetric image data indicative thereof.

An imaging data processor 124 includes a microprocessor 126 and a computer readable storage medium such as memory 128. The memory 128 stores computer executable instructions, which are executable by the microprocessor 126. The imaging data processor 124 is shown separate from the system 100. As such, it can be part of a dedicated workstation, a desk computer, a server, and/or other computing system. In another embodiment, the imaging data processor 124 is part of the console 114.

The instructions include one or more algorithms for processing reconstructed and/or raw imaging data from the system 100 and/or deriving information therefrom. The illustrated memory 128 includes a colonography algorithm 130, a bone mineral density algorithm 132, a fat assessment algorithm 134, an vascular calcium score algorithm 136 and one or more other algorithms 138.

A presentation component 140 presents the processed and/or derived information and/or other information. This may include presenting raw imaging data, reconstructed imaging data, scores, and/or other information. As described in greater detail next, the presentation component 140 can present such information in a graphical user interface (GUI) displayed on a monitor. The computer executable instructions for the GUI 200 can be stored in the memory 128 and/or other storage.

Figure 2:
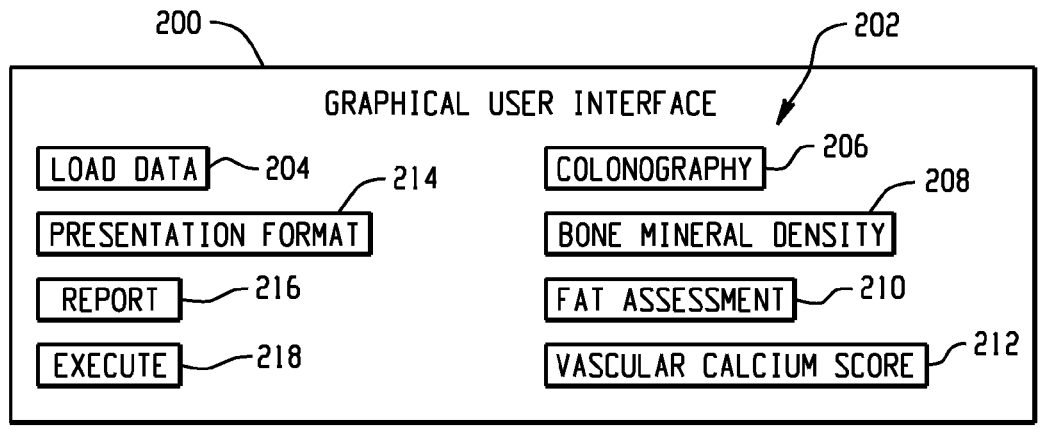
FIG. 2 illustrates an example graphical user interface for presenting the imaging data and/or information derived therefrom.

FIG. 2 illustrates an example GUI 200. The GUI includes one or more user-activated regions 202 that invoke one or more of the algorithms stored in the memory 128. The user-activated regions 202 can be activated via various input devices such as a mouse, a digital pen, a keyboard, a touch screen and/or other input device.

A load data region 204 allows a user to select stored imaging data, including raw and/or reconstructed imaging data, for analysis. Such data can be stored local or remote to the system running the GUI application. By way of example, the data may be stored on a local hard drive, portable storage medium, or a remote data storage repository. Examples of a remote data storage repository include a Picture Archiving and Communication System (PACS), a Radiology Information System (RIS), a Hospital Information System (HIS), and/or other storage, database, and/or archival system. Remotely located data can be received over a network, a bus, or the like.

The illustrated GUI 200 also includes a colonography algorithm invoking region 206, a bone mineral density algorithm invoking region 208, a fat assessment algorithm invoking region 210, and a vascular calcium algorithm invoking region 212. The algorithm invoking region 206-212 are individually selectable by a user. This allows a user the ability to select one or more the type(s) of analysis to perform on the selected raw and/or reconstructed imaging data. For example, if the user desires to perform colonography, bone mineral density, fat assessment and vascular calcium analyses, then the user activates all four to the regions 206-212. If the user desires to perform a subset of colonography, bone mineral density, fat assessment and vascular calcium analyses, then the user activates the regions 206-212 corresponding to the subset. If the user desires to perform another analysis, the user does not activate any of the regions 206-212.

A presentation format region 214 provides options that allow the user to pre-select how and what results of the analysis will be displayed. For instance, the GUI 200 or other window presented on a display can be split into four different windows or screens, one for the results for each of the colonography, bone mineral density, fat assessment and vascular calcium analyses. In another instance, the analysis results for one or more of the algorithms also be presented in a same window. The analysis results may include various information such as, but are not limited to, images (2D, 3D, 4D and/or movie), scores, a combination of images and scores, and/or other information. The GUI 200 may also my associated with a default preference file, which may provide a default presentation format. In this instance, the region 214 can be omitted.

A report user activated region 216 allows the user to indicate whether a report should be generated, what information to include on the report, where to send the report, etc. In one instance, activating the report user activated region 216 generates a window with a list of report options, which are selectable by the user. In another instance, a comprehensive single report that includes results and/or other information about each of the different imaging procedures from the single scan is generated. As such, the imaging data processor 124 can consolidate and integrate the different imaging procedures into a single comprehensive report.

An execute user activated region 218 allows the user to invoke the processor 126 to execute the computer readable instructions corresponding to the selected application regions 206-212.

Figure 3:
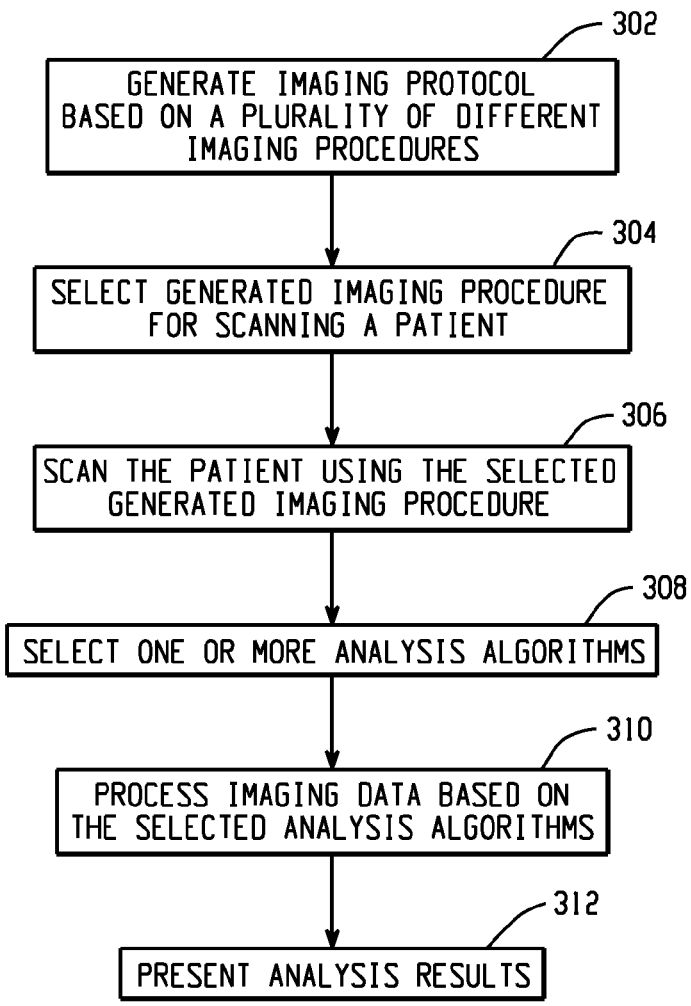
FIG. 3 illustrates an example method.

FIG. 3 illustrates an example workflow.

At 302, an imaging protocol is generated based on a plurality of different imaging procedures. As discussed above, in one instance a protocol is generated and optimized based on a set of imaging procedures including colonography, bone mineral density, fat assessment, and vascular calcium score imaging procedures. In one instance, the imaging protocol includes an abdomen-pelvis scan with parameters optimized for the foregoing imaging procedures. As noted herein, the generated protocol can be associated with information regarding the imaging procedure(s) it satisfies (e.g., for diagnostics, screening or other purposes), stored, and accessible by authorized personnel.

At 304, the imaging protocol is selected for scanning a patient. The selected protocol may be protocol generated for the particular patient and imaging procedure to be performed, a previous scan of the patient, a previous scan of a different patient, or other protocol, as discussed herein.

At 306, the patient is scanned using the selected protocol. Likewise, the resulting imaging data and/or data derived therefrom can be tagged or otherwise associated with information regarding the imaging procedure(s) it satisfies, stored, and accessible by authorized personnel.

At 308, a user selects one or more analysis algorithms, including one or more of colonography, bone mineral density, fat assessment, and vascular calcium score algorithms.

At 310, the imaging data from the scan is processed using the selected one or more analysis algorithms. Likewise, the processed imaging data can be tagged or otherwise associated with information regarding the imaging procedure(s) it satisfies, stored, and accessible by authorized personnel.

At 312, the processing results are presented. As described herein, this may include concurrently presenting information (e.g., images, scores, etc.) for one or more of the different applications in separate or a same sub-windows on the display.

As noted herein, such a protocol allows for analyzing imaging data from a single scan to obtain colonography, bone mineral density, fat assessment, and vascular calcium information.

The above may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

Although the illustrated example is discussed in the context of using CT colonography data for bone mineral density, aortic calcification, and fat analysis, it is to be appreciated that other data can be used additionally or alternatively for bone mineral density, aortic calcification, and fat analysis and/or the CT colonography data captured using the approaches herein can be used for other types of analysis.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   receiving a signal indicative of a single user selected imaging protocol for scanning,
   wherein the imaging protocol includes a weighted aggregate of a colonography procedure and at least one other imaging procedure;
   performing a single scan with an imaging system using the single user selected protocol; and
   generating a single set of image data that includes colonography and bone mineral density data information.

2. The method of claim 1, wherein the at least one other imaging procedure includes a bone mineral density imaging procedure.

3. The method of claim 1, further comprising:
   receiving a signal indicative of one or more user selected analysis algorithms, wherein the one or more user selected analysis algorithms include at least a colonography algorithm; and processing the single set of image data using the colonography algorithm, producing a processing result.

4. The method of claim 3, wherein the processing result includes at least one colonography measurement.

5. The method of claim 1, further comprising:
receiving a signal indicative of one or more user selected analysis algorithms, wherein the one or more user selected analysis algorithms include at least a bone mineral density algorithm; and
processing the single set of image data using the bone mineral density algorithm, producing a processing result.

6. The method of claim 5, wherein the processing result includes at least one of a bone mineral density measurement.

7. The method of claim 1, further comprising:
displaying the single set of image data that includes the colonography and bone mineral density data information in a view port of a graphical user interface.

8. The method of claim 1, wherein at least one of the imaging procedures is a diagnostic imaging procedure.

9. The method of claim 1, wherein at least one of the imaging procedures is a screening imaging procedure.

10. The method of claim 1, wherein the single imaging protocol further includes a parameter for at least one of a fat composition procedure or an aortic calcium imaging procedure.

11. An imaging system, comprising:
a radiation source;
a detector array;
a reconstructor; and
a console configured to control the radiation source, the detector array and the reconstructor to scan an object using scan parameters from a single imaging protocol, wherein the single imaging protocol includes a weighted aggregate of a colonography procedure and at least one other imaging procedures, and further configured to control the reconstructor to generate a single set of image data that includes colonography and bone mineral density data information.

12. The system of claim 11, wherein the at least one other imaging procedure includes a bone mineral density imaging procedure.

13. The system of claim 11, further comprising:
receiving a signal indicative of one or more user selected analysis algorithms, wherein the one or more user selected analysis algorithms include at least a colonography algorithm; and
processing the single set of image data using the colonography algorithm, producing a processing result.

14. The system of claim 13, wherein the processing result includes at least one colonography measurement.

15. The system of claim 11, further comprising:
receiving a signal indicative of one or more user selected analysis algorithms, wherein the one or more user selected analysis algorithms include at least a bone mineral density algorithm; and
processing the single set of image data using the bone mineral density algorithm, producing a processing result.

16. The system of claim 15, wherein the processing result includes at least one of a bone mineral density measurement.

17. The system of claim 11, further comprising:
displaying the single set of image data that includes colonography and bone mineral density data information in a view port of a graphical user interface.

18. The system of claim 11, wherein at least one of the imaging procedures is at least one of a diagnostic imaging procedure or a screening imaging procedure.

19. The system of claim 11, wherein the single imaging protocol further includes a parameter for at least one of a fat composition procedure or an aortic calcium imaging procedure.

20. A memory containing instructions which, when executed by a computer, cause the computer to perform the steps of:
perform a single scan with an imaging system based on a single user selected imaging protocol, wherein the imaging protocol includes a weighted aggregate of a colonography procedure and at least one other imaging procedure; and
generate a single set of image data that includes colonography and bone mineral density data information.

* * * * *